United States Patent [19]

Fontanella et al.

[11] 4,011,238
[45] Mar. 8, 1977

[54] 2-IMIDAZOLIDIONE DERIVATIVES

[75] Inventors: Luigi Fontanella; Guilio Maffii, both of Milan, Italy

[73] Assignee: Gruppo Lepetit S.p.A., Milan, Italy

[22] Filed: July 7, 1975

[21] Appl. No.: 593,358

Related U.S. Application Data

[63] Continuation of Ser. No. 367,675, June 6, 1973, abandoned.

[30] Foreign Application Priority Data

July 26, 1972 Italy .................................. 27404/72

[52] U.S. Cl. ............................. 260/309.7; 424/273
[51] Int. Cl.² ........................................ C07D 403/06
[58] Field of Search ................................ 260/309.7

[56] References Cited
UNITED STATES PATENTS 3,196,152  7/1965  Wright et al. .................. 260/247.2

*Primary Examiner*—Natalie Trousof
*Attorney, Agent, or Firm*—Theodore Post; C. Kenneth Bjork

[57] ABSTRACT

Imidazolidinone derivatives of the formula

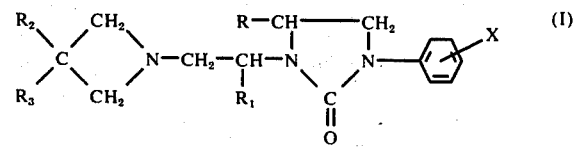

where R, $R_1$, $R_2$ and $R_3$ independently are hydrogen or lower alkyl, X represents one or two substituents selected from the group lower alkyl, halo, lower alkoxy, trifluoromethyl, and their pharmaceutically-acceptable acid salts.

The compounds are prepared essentially by the method described by Wright in J. Med. Chem. 9, 852 (1966). The compounds have high depressant activity on the central nervous system.

3 Claims, No Drawings

2-IMIDAZOLIDIONE DERIVATIVES

This is a continuation, of application Ser. No. 367,675 filed June 6, 1973 now abandoned

BACKGROUND OF THE INVENTION

In the prior art there are described imidazolidinone derivatives having an aryl group on one nitrogen atom and an amino-lower alkyl group on the other nitrogen atom; South African Patent No. 62/4312. Other imidazolidinone derivatives where the aminic group is represented by a radical

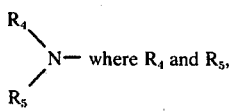

besides being lower alkyl, can also represent, taken together with the nitrogen atom, a heterocyclic 5- to 7-membered ring, are also known; ibid.

W. B. Wright et al., J. Med. Chem. 9, 852, 1966, report the results of pharmacological tests on a series of compounds of the class covered by the above-mentioned South African Patent and point out that 1-(m-chlorophenyl)-3-(2-dimethylaminoethyl)-2-imidazolidinone (imidoline) is the most promising one from the biological point of view.

It has now surprisingly been found that the introduction of an azetidine ring leads to imidazolidinone derivatives much more active than those described in the literature.

SUMMARY OF THE INVENTION

The present invention relates to new imidazolidinone derivatives represented by the formula

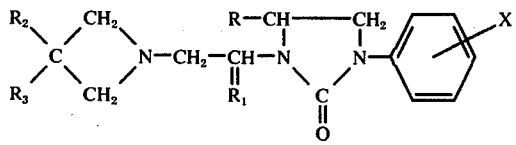

wherein R, $R_1$, $R_2$ and $R_3$ independently represent hydrogen or a lower alkyl group of 1, to 2, to 3, to 4 carbon atoms, X represents one or two substituents selected from the group of lower alkyl of from 1 to 2, to 3, to 4 carbon atoms, halo, lower alkoxy, trifluoromethyl, and their pharmaceutically acceptable acid salts.

In the specification and claims, the term "lower alkoxy" designates an alkoxy group having from 1, to 2, to 3, to 4 carbon atoms, and the term "halo" designates chloro, bromo or fluoro.

DESCRIPTION OF THE PREFERRED EMBODIMENTS

It has now surprisingly been found that the introduction of an azetidine ring as in compounds of formula (I) leads to imidazolidinone derivatives much more active than those described in the literature. A method for the preparation of the inventive compounds is based essentially on that described by W. B. Wright, et al., J. Med. Chem. 9, 852 (1966). In their preparation, imidazolidinones represented by the formula

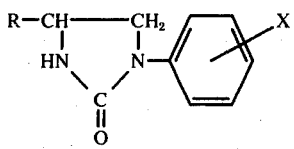

are alkylated in the presence of a strong base, e.g., an alkali metal hydroxide or alkoxide with a β-haloethylazetidine derivative represented by the formula

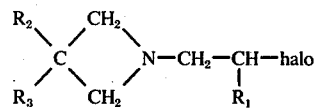

wherein R, $R_1$, $R_2$, $R_3$ and X have the same meaning as given previously and halo represents bromo or chloro. The alkylation conditions are essentially the same as those described in the paper cited. The azetidine derivatives of formula (III) are prepared by the method of E. Testa et al., Liebigs Ann. Chem 635, 119 (1960).

An alternative method for the preparation of the inventive compounds comprises reacting an imidazolidinone derivative represented by formula (IV) with an azetidine according to the following scheme:

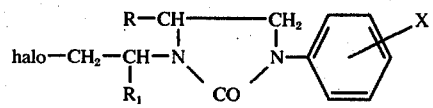

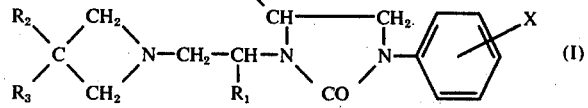

wherein R, $R_1$, $R_2$, $R_3$ and X have the same meaning as previously given and halo represents bromo or chloro. The azetidines employed are prepared by the method of E. Testa et al., Liebigs Ann. Chem. 633, 56, (1960). The haloethylimidazole derivative of formula (IV) are prepared through cyclization of a 2-(2-(phenylamino)ethylamino) alkanol of formula (V) with phosgene followed by alkaline hydrolysis of the so-obtained product and substitution of the hydroxy group with a halo group by reaction with a thionyl halide according to the following equations:

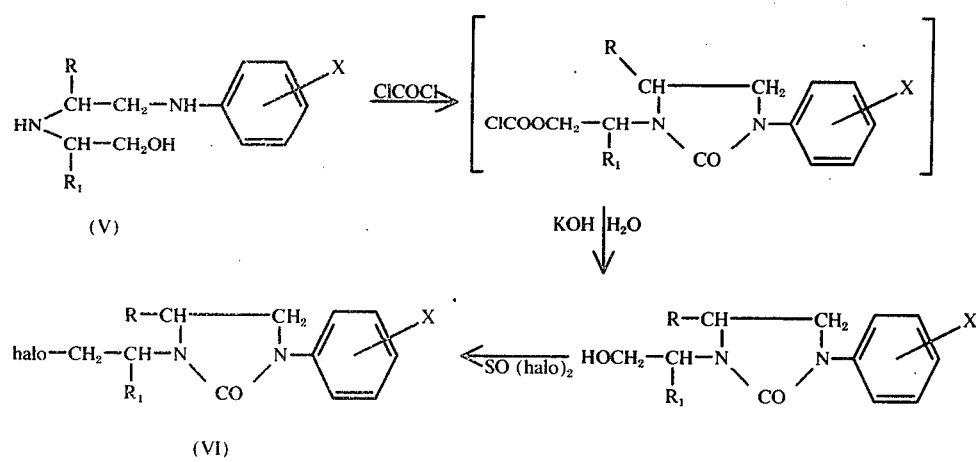

wherein R, R₁, R₂, R₃, halo and X have the same meaning as previously given.

Instead of using the free alcohol of formula (V), the corresponding acetate also can be employed.

The aminoalkanols of formula (V) are obtained by reduction of a 2-[1-(phenylcerbamyl)alkylamino]alkanoic acid ester with a mixed alkali metal hydride. The alcohol acetates are prepared pursuant to known acylation procedures. The alkanoic acid esters are in turn prepared by the method of Fontanella e.a., Farmaco, Ed. Sci. 25, 542(1970).

The products of the invention are generally solids moderately soluble in water and highly soluble in dilute acids or in common organic solvents.

The following examples further describe the invention and manner and process of making and using it to enable the art skilled to make and use the same, and set forth the best modes contemplated by the inventors of carrying out the invention.

EXAMPLE 1:
1-(m-Chlorophenyl)-3-[2-(3,3-dimethylazetidin-1yl)-ethyl]-2-imidazolidinone A solution of 5 g. of 1-(m-chlorophenyl)-2-imidazolidinone in 30 ml. of dimethylformamide is added at room temperature to a mixture of 1.5 g. of 50% NaH (as a mineral oil emulsion) in 30 ml. of dimethylformamide. The reaction mixture is stirred for an hour at room temperature and 4.5 g. of 3,3-dimethyl-1-(2-chloroethyl)azetidine is added thereto. The mixture is then stirred at room temperature for an additional two hours, then heated for five hours at 80°–85° C. The by-product salts are filtered off and the solvent is removed under vacuum. The residue is taken up with 8 ml. of aqueous 18% HCl and 16 ml. of water and extracted with ether. The water solution is alkalinized by adding aqueous 15% sodium carbonate and extracted with diethyl ether. By evaporation of the organic layer, a residue is obtained that is triturated in light petroleum. Yield 7.24 g., m.p. 84°–85° C. (from hexane). The hydrochloride melts at 191°–192° C.

EXAMPLES 2–3:

Pursuant to the procedure of the previous Example and using a predetermined 3,3-dialkyl-1-(2-chloroethyl)-azetidine, the following compounds are prepared:

2. 1-(m-chlorophenyl)-3-[2-(3,3-dipropylazetidin-1-yl)-ethyl]-2-imidazolidinone, m.p. 100°–102° C.; by reacting 1-(m-chlorophenyl)-2-imidazolidinone with 3,3-dipropyl-1-(2-chloroethyl)azetidine.

3. 1-(m-chlorophenyl)-3-[2-(3,3-dibutylazetidin-1-yl)-ethyl]-2-imidazolidinone, m.p. 85° C., by reacting 1-(m-chlorophenyl)-2-imidazolidinone and 3,3-dibutyl-1-(2-chloroethyl)azetidine.

EXAMPLE 4:
1-(m-Chlorophenyl)-4-methyl-3-[2-(3,3-dipropylazetidin-1-yl)-1-methylethyl]-2-imidazolidinone A mixture of 7 g. of 3-(2-chloro-1-methylethyl)-1-(m-chlorophenyl)-4-methyl-2-imidazolidinone and 10 g. of 3,3-dipropylazetidine in 100 ml. of anhydrous benzene is heated in a bomb at 150°–160° C. for 8 hours. The solvent is evaporated under vacuum and the residue is taken up with water, alkalinized with aqueous sodium carbonate and extracted with diethyl ether. The residue obtained by evaporation of the organic layer is purified by column chromatography through silica gel, using as the eluent chloroform containing 8% of methanol. Yield 8.6 g., b.p. 220° C./0.5 mm Hg.

EXAMPLE 5:
1-(p-Chlorophenyl)-4-methyl-3-[2-(3,3-dipropylazetidin-1-yl)-1-methylethyl]-2-imidazolidinone By substituting 3-(2-chloro-1-methylethyl)-1-(p-chlorophenyl)-4-methyl-2-imidazolidinone in place of 3-(2-chloro-1-methylethyl)-1-(m-chlorophenyl)-4-methyl-2-imidazolidinone in the procedure of Example 4, the title compound is obtained. B.p. 160° C./0.6 mm Hg.

EXAMPLE 6:
1-(m-Chlorophenyl)-4-methyl-3-[2-(3,3-dimethylazetidin-1-yl)-1-methylethyl]-2-imidazolidinone The title compound is prepared pursuant to the procedure of Example 4 from 3,3-dimethylazetidine and 3-(2-chloro-1-methylethyl)-1-(m-chlorophenyl)-4-methyl-2-imidazolidinone. B.p. 200° C./0.6 mm Hg. The corresponding hydrochloride melts at 162°–164° C.

EXAMPLE 7

Pursuant to the procedure of E. Testa et al., Liebigs Ann. Chem. 635, 119, (1960), the following intermediate compounds are prepared:

1-(2-chloroethyl)-3,3-dipropylazetidine hydrochloride. M.p. 178°–179° C.

1-(2-Chloroethyl)-3,3-dibutylazetidine hydrochloride. M.p. 188°–189° C.

EXAMPLE 8:

2-[(2-(p-Chlorophenyl)amino-1-methylethyl]-amino)-1-propanol

95 Grams of 2-[1-(p-chlorophenylcarbamyl)ethylamino]-propionic acid ethyl ester dissolved in 1200 ml. of anhydrous diethyl ether is gradually added under stirring to a suspension of 38 g. of $LiAlH_4$ in 2000 ml. of diethyl ether cooled to 0° C. The reaction mixture is refluxed for two hours with stirring, then the reaction complex is decomposed at 0° C. with water, stirred for 30 minutes at room temperature and the inorganic solids separated by filtration. The ether solution is dried and evaporated, and the residue, distilled in a bulb, yields 76 g. of the title compound. B.p. 170° C./0.4 mm Hg. yield 98.5%. The corresponding acetate, obtained by treatment of the title compound with acetyl chloride in acetic acid, boils at 160° C./0.5 mm Hg. In the same way, the corresponding m-chlorophenyl-substituted derivative is synthesized. B.p 170° C./0.5 mm Hg. The corresponding acetate boils at 160° C./0.5 mm Hg.

EXAMPLE 9:

1-(p-Chlorophenyl)-3-(1-(hydroxymethyl)ethyl)-4-methyl-2-imidazolidinone

To a mixture of 36 g. of 2-[2-(p-chlorophenyl) amino-1-methylethyl] amino-1-propanol in 75 ml. of toluene and 29 g. of KOH in 250 ml. of $H_2O$ cooled to 0° C., a solution of 22 g. of phosgene in 75 ml. of anhydrous toluene is added. The mixture is stirred for 90 minutes and the reaction is kept alkaline by adding an aqueous solution of KOH. The toluene is separated and the aqueous phase is extracted with diethyl ether. The organic solutions, collected and dried, are evaporated and the residue is dissolved in 500 ml. of methanol and treated with 2.5 g of KOH. After standing for two hours and evaporation under vacuum of the methanol, the residue is taken up with water and acidified with aqueous dilute hydrochloric acid. After extraction with ether, the residue obtained by evaporation of the solvent is purified by column chromatography through silica gel and eluting with chloroform containing 1% of methanol. The fractions containing the product are collected and evaporated; the residue is washed with a small amount of isopropyl ether, filtered and washed with light petroleum. Yield 15.2 grams (38%) of the title product, m.p. 108°–110° C. In the same way, the m-chloro-substituted analog is prepared in a 63% yield. M.p. 75°–77° C.

EXAMPLE 10:

1-(p-Chlorophenyl)-3-(2-chloro-1-methylethyl)-4-methyl-2-imidazolidinone

To a solution of 16 g. of 1-(p-chlorophenyl)-3-(1-(hydroxymethyl)ethyl)-4-methyl-2-imidazolidinone in 400 ml. of anhydrous chloroform, 14.5 g. of $SOCl_2$ is added dropwise with stirring while the temperature is maintained at 0° C. The mixture is then refluxed for 45 minutes, concentrated under vacuum and taken up with benzene, then evaporated to dryness again, yielding 15.1 grams (94%) of the title compound, m.p. 70°–72° C. (from diisopropyl ether). The corresponding m-chlorophenyl-substituted compound is prepared in the same way. Yield 97%, b.p. 200° C./0.5 mm Hg.

Pursuant to procedures previously described, the following compounds of formula (I) wherein R, $R_1$, $R_2$, $R_3$ and X have the indicated meaning can be prepared:

$$R_2 \diagdown \diagup CH_2 \diagdown \diagup N-CH_2-CH-N \diagdown \diagup \diagdown \diagup -X$$
(structural formula with imidazolidinone ring)

| R | $R_1$ | $R_2$ | $R_3$ | X |
|---|---|---|---|---|
| $CH_3$ | H | $CH_3$ | $CH_3$ | m-Cl |
| $C_2H_5$ | H | $CH_3$ | $CH_3$ | m-Cl |
| iso-$C_3H_7$ | H | $CH_3$ | $CH_3$ | m-Cl |
| H | H | $CH_3$ | $CH_3$ | 3,4-$Cl_2$ |
| H | H | H | H | m-$OCH_3$ |
| H | $CH_3$ | H | H | m-Cl |
| H | H | H | H | m-F |
| H | H | $CH_3$ | $CH_3$ | m-$CF_3$ |
| $CH_3$ | $CH_3$ | $CH_3$ | $CH_3$ | m-$CH_3$ |
| H | H | $CH_3$ | $CH_3$ | o-Cl |

The new imidazolidinones all have a very high depressant activity on the central nervous system of animals. Representative of such activity, pharmacological data of 1-(m-chlorophenyl)-3-[2-(3,3-dimethylazetidin-1-yl)ethyl]-2-imidazolidinone, "A" below, in comparison with the art compound 1-(m-chlorophenyl)-3-(2-dimethylaminoethyl)-2-imidazolidinone (imidoline) and with the art compound chlorpromazine (CPZ) are hereinbelow reported:

| | A | Imidoline | CPZ |
|---|---|---|---|
| $LD_{50}$, rat, mg/kg i.p. | 200 | 200 | 120 |
| $CR_2$ ($ED_{50}$ rat, mg/kg i.p.) | 0.25 | 2.5 | 0.96 |
| CR ($ED_{50}$ rat, mg/kg i.p.) | 0.50 | 5–10 | 3.95 |
| Apomorphine emesis ($ED_{50}$, dog, γ/kg i.p.) | <50 | 250 | 1000 |

The symbols CR and $CR_2$ relate, respectively, to the tests of inhibition of the primary and secondary conditioned response according to the method of L. Cook et al., Ann. N.Y. Acad. Sci. 66, 740, (1957), as modified by Maffii et al., J. Pharm. Pharmacol. 11, 129 (1959). The inhibition of apomorphine emesis test in the dog is carried out according to the method of G. Chen. et al., J. Pharm. Exptl. Therap, 98, 245 (1950). These parameters are of great importance in the characterization of a major tranquilizer and, therefore, the results obtained are highly significant, since they show a remarkable superiority of the new derivative.

Besides the more specific activity on the conditioned behavior and the more potent anti-emetic effect, the compound "A" shows another favorable characteristic in comparison with chlorpromazine, much lower side effects on the cardiovascular system as evidenced at a dose level which is 5 to 10 times higher than that of chlorpromazine.

The inventive compounds may be incorporated as the principal active components in various therapeutic compositions which are prepared in a wide variety of forms, such as compressed or coated tablets, soft and hard gelatin capsules, delayed-release tablets, suspensions and other liquid preparations suitable for oral or parenteral use. For example, 5 mg. of 1-(m-chlorophenyl)-3-[2-(3,3-dimethylazetidin-1-yl)ethyl]-2-imidazolidinone is blended with a carrier composed of lactose, corn starch, stearic acid and talc in a compressed tablet to provide a very satisfactory dosage unit form. Where desired, excipients, binders, extenders, adjuvants, flavoring materials and the like are incorporated.

The preferred pharmaceutical carriers or diluents are non-toxic solids, such as starch, dextrose, lactose, acacia, talc, stearic acid, magnesium stearate, tragacanth and the like.

Where therapeutic compositions are prepared in such dosage unit forms as elixirs, suspension and as liquid preparations for parenteral use, non-toxic liquid carriers or diluents are utilized, such as water, alcohol, glycerine, sorbitol and the like.

The usual therapeutic dosage varies from about 0.01 to about 5 mg. per kilogram of body weight.

What is claimed is:
1. A compound represented by the formula

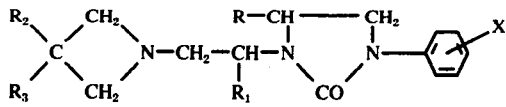

wherein R and $R_1$ independently represent H or lower alkyl, and $R_2$ and $R_3$ independently represent lower alkyl, X represents one or two substituents selected from lower alkyl, halo, lower alkoxy or trifluoromethyl, or a salt thereof with a pharmaceutically-acceptable acid.

2. The compound of claim 1 which is 1-(m-chlorophenyl)-3-[2-(3,3-dimethylazetidin-1-yl)-ethyl]-2-imidazolidinone.

3. The compound of claim 1 which is 1-(m-chlorophenyl)-4-methyl-3-[2-(3,3-dimethylazetidin-1-yl)-1-methylethyl]-2-imidazolidinone.

* * * * *

UNITED STATES PATENT AND TRADEMARK OFFICE
CERTIFICATE OF CORRECTION

PATENT NO. : 4,011,238
DATED : March 8, 1977
INVENTOR(S) : Luigi Fontanella & Guilio Maffii It is certified that error appears in the above-identified patent and that said Letters Patent are hereby corrected as shown below:

Title page, item [54], "2-IMIDAZOLIDIONE DERIVATIVES" should read -- 2-IMIDAZOLIDINONE DERIVATIVES --.

Column 1, line 1, same title correction as above.

Column 1, lines 40 - 47, the formula should read:

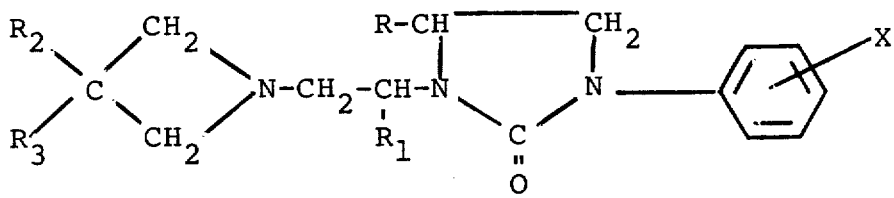

Column 3, line 41, the title of EXAMPLE 1,
"1-(m-Chlorophenyl)-3-[2-(3,3-dimethylazetidin-1yl)-" should be
-- 1-(m-Chlorophenyl)-3-[2-(3,3-dimethylazetidin-1-yl)- --.

Signed and Sealed this

Fourth Day of October 1977

[SEAL]

Attest:

RUTH C. MASON
Attesting Officer

LUTRELLE F. PARKER
Acting Commissioner of Patents and Trademarks